United States Patent
Dor et al.

(10) Patent No.: US 10,187,742 B2
(45) Date of Patent: Jan. 22, 2019

(54) SYSTEM AND METHOD FOR TRACKING AND MONITORING SURGICAL TOOLS

(71) Applicant: HALDOR ADVANCED TECHNOLOGIES LTD, Hod HaSharon (IL)

(72) Inventors: Guy Dor, Rosh Haayn (IL); Dan Zeeli, North York (CA); Ilan Kadosh-Tamari, Ramat Hasharon (IL)

(73) Assignee: HALDOR ADVANCED TECHNOLOGIES LTD, Hod HaSharon (IL)

( * ) Notice: Subject to any disclaimer, the term of this patent is extended or adjusted under 35 U.S.C. 154(b) by 113 days.

(21) Appl. No.: 14/599,589

(22) Filed: Jan. 19, 2015

(65) Prior Publication Data
US 2016/0212577 A1 Jul. 21, 2016

(51) Int. Cl.
*H04W 4/02* (2018.01)
*G06F 17/30* (2006.01)
(Continued)

(52) U.S. Cl.
CPC ........ *H04W 4/02* (2013.01); *G06F 17/30377* (2013.01); *G06F 17/30483* (2013.01);
(Continued)

(58) Field of Classification Search
CPC ................ H04W 4/02; G06F 17/30377; G06F 17/30483
See application file for complete search history.

(56) References Cited

U.S. PATENT DOCUMENTS

| 7,268,684 B2 | 9/2007 | Tethrake et al. |
| 7,518,502 B2 | 4/2009 | Austin et al. |

(Continued)

FOREIGN PATENT DOCUMENTS

| DE | 10014542 | 10/2001 |
| WO | 2012146867 | 11/2012 |

OTHER PUBLICATIONS http://www.rfidjournal.com/articles/view?10391 Innovapaedics Develops RFID System for Tracking Surgical Implants, Tools by Claire Swedberg. Feb. 5, 2013.
(Continued)

*Primary Examiner* — Patrick Edouard
*Assistant Examiner* — Eboni Hughes
(74) *Attorney, Agent, or Firm* — Soroker Agmon Nordman

(57) ABSTRACT

A system for monitoring and tracking location of a tag paired to a tool is disclosed, the system comprising a communication unit to receive flag event data, the flag event data relating to a detected event, the flag event data including at least tag identification data, location data of the tag, detected event type, and time of occurrence of the detected event. The system comprises a storage unit to store data records of tags, the data records comprising a current tag location and data relating to the tool which is paired to the tag, and to store a set of instructions defined for handling flag event data. The system comprises a processing unit to receive flag event data, and to transmit a notification of the flag event data to other connected devices according to the stored set of instructions for handling the flag event data. The processing unit may be configured to identify a monitoring station located at a current location of the tool paired to the tag, and to transmit a notification related to the flag event data to the identified monitoring station.

13 Claims, 6 Drawing Sheets

(51) Int. Cl.
*G06Q 10/08* (2012.01)
*G06Q 50/22* (2018.01)
*A61B 90/98* (2016.01)
*A61B 90/00* (2016.01)

(52) U.S. Cl.
CPC ............ *G06Q 10/087* (2013.01); *A61B 90/98* (2016.02); *A61B 2090/0805* (2016.02); *G06Q 50/22* (2013.01)

(56) References Cited

U.S. PATENT DOCUMENTS

| | | | |
|---|---|---|---|
| 7,701,334 B1* | 4/2010 | Perkins | G06F 19/327 340/539.13 |
| 8,624,721 B2 | 1/2014 | Barker, Jr. | |
| 2004/0174264 A1 | 9/2004 | Reisman et al. | |
| 2007/0094303 A1* | 4/2007 | Zwingenberger | A61L 2/24 |
| 2008/0030345 A1* | 2/2008 | Austin | A61B 90/90 340/572.8 |
| 2008/0055109 A1* | 3/2008 | Freathy | G07C 9/00111 340/8.1 |
| 2010/0036755 A1 | 2/2010 | Saghbini | |
| 2012/0169470 A1 | 7/2012 | Lee | |
| 2013/0106607 A1 | 5/2013 | Clement et al. | |
| 2013/0325495 A1 | 12/2013 | Hempstead et al. | |
| 2013/0336554 A1* | 12/2013 | Lewis | G06K 9/00771 382/128 |
| 2014/0263633 A1* | 9/2014 | Schmucker | G06Q 10/0875 235/385 |

OTHER PUBLICATIONS http://www.wirelessintegrated.com/automated-instrument-tracking-system-surgicalinstrument-tracking-system.html Automated Instrument Tracking System—Surgical Instrument Tracking System.

Kazuhiko Yamashita et al; Identification of Information Surgical Instrument by Ceramic RFID Tag, Automation Congress, 2008. WAC 2008. Word, IEEE, Piscataway, NJ, USA, Sep. 28, 2008.

Meiller Y et al, RAFID-Embedded Decision Support for Tracking Surgical Equipment. System Sciences (HICSS), 2011 44th Hawaii International Conference on, IEEE, Jan. 4, 2011.

* cited by examiner

SYSTEM AND METHOD FOR TRACKING AND MONITORING SURGICAL TOOLS

FIELD OF THE INVENTION

The subject matter relates generally to a system and method for real time tracking of one or more surgical tools across one or more locations.

BACKGROUND OF THE INVENTION

Some perioperative related situations, such as infection control scenarios, require the recalling of surgical instruments, items, and disposables (referred to as "tools" herein) that were affected by the perioperative situation. For example, surgical tools that may be the cause of a patient contracting Creutzfeldt-Jakob disease ("CJD"), or other hospital-contracted infections, due to improper cleaning, handling and sanitizing. Regulating and participating entities, such as regulatory bodies, hospitals, reprocessing facilities, medical device manufacturers, and surgical instrument manufacturers must be able to promptly locate the current location of the surgical tools and also know their previous locations, i.e. where the specific surgical instrument, item, or disposable traveled until arriving at its current location. Infection control entities, such as the Centers for Disease Control and Prevention ("CDC"), Social Accountability Accreditation Services ("SAAS"), Food and Drug Administration ("FDA"), or the like, must be notified as quickly as possible after the occurrence of the perioperative situation to provide quick and efficient solutions and prevent further incidents. Thus, it is desirable to provide a solution for efficient monitoring and tracking of tools, in case an infection control or disease control event is detected.

SUMMARY

A computerized system is disclosed, to track and monitor a tag paired to a tool, e.g. a surgical instrument, item or disposable. The system may include a signal receiving unit to obtain a location of a tag, a central server comprising or operationally connected to a tag database configured to store a data record of the tag, wherein the data record comprises information about the tag, and a tag processing unit configured to update the data record stored in the tag database.

A monitoring station may be included in the system, to obtain a flag event related to the tag, the flag event including an indication that the tool paired to the tag was present in a location of a detected event. The monitoring station may transmit the flag event to the central server. The computerized system may comprise a communication unit to transmit the flag event data to a current and/or past location of the tag, or the tool paired to the tag. A flag event may comprise tag identification data. In some cases, the tag may be paired to a set of tool.

Embodiments of the disclosed subject matter include a method of tracking and monitoring a tag paired to a tool, the method comprising receiving a signal including location data related to the tag, wherein the signal comprises tag identification data; storing the received location data in a tag database as part of a data record relating to the tag, based on the tag identification data; receiving a flag event for the tag, wherein the flag event comprises tag identification data, flag event including an indication that the tool paired to the tag was present in a location of a detected event that triggered the flag event; and transmitting the flag event to a current location of the tag which is retrieved from the stored data record.

In some embodiments, the tag data record stored in the tag database may be updated with event flag data. One or more tags associated with the received tag identity data may be determined or sought, the associated tags including tags which participated in the detected event. The event flag data or portions thereof may be transmitted to a current location of the one or more associated tags, based on the current locations of the associated tags stored in the tag database. Additional tag data records in the tag database may be updated according to the flag event data.

A flag removal event may be received, to remove a flag event from the tag data record, or update the data record that the flag event is completed, handled or no longer relevant. The flag removal event may include tag identification data. The tag data record stored in the tag database may be updated according to the flag removal event. A computerized monitoring station may transmit the flag event data and/or the flag event removal data.

A computerized system for monitoring and locating tools is disclosed, comprising an antenna for obtaining a location of a tag, wherein the tag is an RFID enabled transponder paired to at least one tool, wherein the antenna receives a signal transmitted from the tag, the signal comprising tag identity data. The signal received from the antenna may be an RFID signal of tags paired to at least one tool.

The computerized system further comprises a monitoring station for obtaining flag event data related to the tag, the flag event data comprising an indication that the tag was present in a location of a detected event. A server may be included in the computerized system, to store a location of the tag in a tag database. The tag database is configured to store a data record of the tag, wherein the record data comprises information related to the tag. The server comprises a processor, the processor configured to determine a current and/or past location of the tag according to the data record of the tag.

The processor may be configured to determine a current location of a staff member who participated in a detected event, and/or to notify the staff member regarding the detected event.

The server may be configured to determine tags which are associated with the flag event, and to send a notification to a monitoring station where tags which are associated with the flag event are currently located.

A system for monitoring and tracking location of a tag paired to a tool is disclosed, the system comprising a communication unit to receive flag event data, the flag event data relating to a detected event, the flag event data including at least tag identification data, location data of the tag, detected event type, and time of occurrence of the detected event. The system comprises a storage unit to store data records of tags, the data records comprising a current tag location and data relating to the tool which is paired to the tag, and to store a set of instructions defined for handling flag event data. The system comprises a processing unit to receive flag event data, and to transmit a notification of the flag event data to other connected devices according to the stored set of instructions for handling the flag event data. The processing unit may be configured to identify a monitoring station located at a current location of the tool paired to the tag, and to transmit a notification related to the flag event data to the identified monitoring station.

BRIEF DESCRIPTION OF THE DRAWINGS

Exemplary non-limited embodiments of the disclosed subject matter will be described, with reference to the following description of the embodiments, in conjunction with the figures. The figures are generally not shown to scale and any sizes are only meant to be exemplary and not necessarily limiting. Corresponding or like elements are optionally designated by the same numerals or letters.

DETAILED DESCRIPTION

Figure 1:
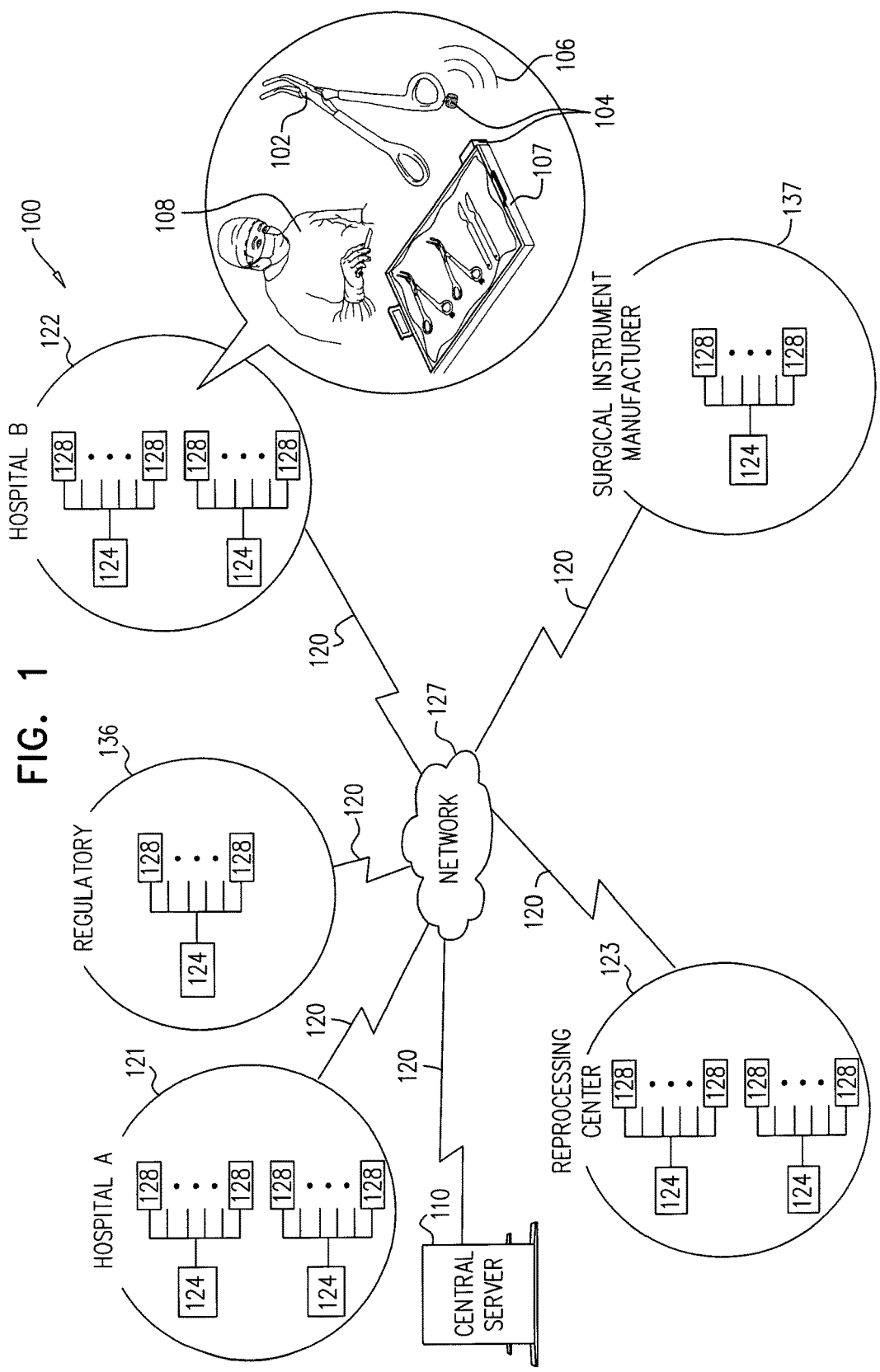
FIG. 1 shows a computerized system for monitoring and tracking a tag associated with a tool or a set of tools at one or more locations, according to some exemplary embodiments of the subject matter.

The subject matter discloses a system and method for real time tracking and monitoring surgical tools and perioperative events across one or more locations, according to exemplary embodiments.

Recall management of surgical tools results from the detection of an infection control scenario (for example, the detection of a CJD scenario) or the suspicion of an infection control scenario. Upon such occurrences, hospitals, instrument manufacturers, and regulatory bodies require the ability to match the surgical tool to the following: a detected event such as a CJD scenario, an infected procedure, or a suspected infected procedure; the surgical tools that were located and/or used during the specific event; and the current location of the event's surgical tools used or located in the same room during the detected event. The event may be declared or discovered a significant time after its occurrence, for example hours, days, or weeks after the event took place. The surgical tools used during the event or which were present at the location and occurrence of that event may have been transferred elsewhere; possible locations may include: the same medical facility where the event occurred, returned to a manufacturer facility, in-route or at a different location (e.g. a different hospital) to be used in a new medical procedure or having been already used in a medical procedure. Efficient and accurate recall management requires determining the chain of events from the occurrence of the event and documenting any treatment or maintenance of the surgical tool.

Maintenance of surgical tools can be costly for an institution such as a medical clinic, hospital, or the like. One cost-effective solution is renting tools from lending companies, or from a different institution; however, the renting and lending of tools may complicate the monitoring and tracking of the tools. As tools from one institution are used alongside tools from other institutions or from a third party, tracking the maintenance record of those tools is further complicated as they are transferred between various locations. Surgical tools undergo rigorous maintenance to ensure they are safe to use; for example, surgical instruments require various washing and sterilization procedures according to the maintenance required after use in a medical procedure. In some cases, due to human error or some other error, the maintenance of the tools may be improper.

Thus monitoring and tracking becomes even more critical when the tools are improperly maintained and then moved around both within an institution and between multiple institutions. When the tools are improperly cleaned, washed, sterilized, etc., they risk causing contaminations, infections, and other hazardous events. For example, use of surgical instruments improperly maintained raises the risk of medical complications during or after a surgical procedure. Improper monitoring and tracking of the tools may lead to the use of tools that are improperly maintained, specifically when the tool is rented or lent and an insufficient maintenance record is provided for the tool.

One technical problem dealt with by the disclosed subject matter is providing a real time notification that one or more tools are contaminated and use of the one or more tools should be avoided. Another technical problem dealt by the disclosed subject matter is real time monitoring and tracking of one or more tools or one or more sets of tools during transfer between one or more locations. Lack of proper monitoring and tracking of the one or more tools may result in a tool of the one or more tools being contaminated and hazardous for use at some other location.

One technical solution according to the disclosed subject matter is using tags paired with, associated with, embedded in or connected to a tool or set of tools to monitor and track the location of the tool or set of tools across the one or more locations. For example, the tags may communicate utilizing radio frequency identification (e.g. "RFID"), Wi-Fi, Bluetooth, QR, near field communication ("NFC"). In some embodiments, the tools may be marked using barcode, laser etching, embedded technology (within the tool) or any other means of marking a tool, and may be scanned manually or automatically as they pass through or near a signal receiving unit.

A signal receiving unit, as referred to herein, may include an antenna, a barcode reader, a Wi-Fi station, or any other communication software and/or hardware which may obtain monitoring data, including location data and/or identification data, from a tag associated with one or more tools, and transfer the monitoring data to a monitoring station and/or to a central server, which are operationally connected to the signal receiving unit via a computerized network.

A tag paired to a tool, as referred to herein, includes a tag associated with, embedded in, or connected to a tool or to set of tools.

In each location of the one or more locations a monitoring station is provided, which receives the real time monitoring data from one or more signal receiving units, for example regarding a current location of a tool or set of tools. The monitoring station updates the central server with the real time monitoring data. The connection between the monitoring stations and the central server may be a remote connection, e.g. web-based, cloud-based, or using secure VPN communication to the central server location. The monitoring data may be continuously or repeatedly updated, whenever the tag paired to the tool or set of tools is detected by a signal receiving unit, e.g. an antenna unit or barcode reader or other code scanner.

Another technical solution according to the disclosed subject matter is updating a central server with data of an event relating to a tool or a set of tools, and providing real time notifications to a user of the tool or set of tools associated with a tag. The real time notification may be or may include an indication regarding tools or instruments that require a special cleaning or sanitizing process, or that need to be discarded. Placement of signal receiving units in predetermined locations near possible locations of events enables scanning and tracking the tags associated with tools (e.g. RFID tags or other means of marking the tools) and determining which tools and/or disposables were present in the vicinity of the event location during the time of occurrence of the event.

The disclosed subject matter relates to recording the movements of tools, specifically surgical instruments that are sent through, to and from medical facilities, e.g. hospitals. Specifically, the subject matter relates to matching an infection control event and data record of the tag with current and previous locations of the tools which were present in the event location during the time of the event, by using autoclavable (e.g., can endure automatic cleaning of instruments in the disinfection machines), non-removable tags, and/or autoclavable embedded tags, and tag readers. The tags and the central computerized system enable wired or wireless data communication with any medical facility and healthcare regulatory communication systems, and a centralized matching database.

The central server performs correlating or matching of data relating to a detected event, such as an infection control event, disease control event, epidemiologic event, emergency event, or other abnormal event relating to health and regulation with the tool/s (e.g. surgical instrument, surgical item, and disposables) which were located in the same location at the time of the infection control event. The subject matter relates to a detected event, tool, and a location matching database system that provides the location data for healthcare systems and healthcare regulatory bodies. When one of a group of predetermined events is detected or determined, a certain protocol or set of actions may need to be followed. For example, in a detected infection control event which was determined to occur at a certain operation room, it is critical to determine who handled the instrument during the detected event occurrence, whether a specific instrument is expected to be infected. Further actions related to the event may include, for example, instructions for packaging or handling the contaminated tool (e.g. prohibiting to pack it in a set).

In the context of this application, a detected event is or includes an infection control event, a disease control event, an epidemiologic event, an emergency event, or any other abnormal event relating to health control and regulation. The detected event may be a surgical operation or medical procedure, that was identified as having a risk of infection, or in which the participating patient was suspected to have an infection or a certain medical condition that may be highly contagious. Examples of detected events include, but are not limited to: a medical procedure in which the patient was determined to carry CJD disease, an infection control scenario which occurred during a surgical operation, an infectious disease which was determined after a surgical operation, a tool which was not sanitized properly, etc. In some cases, even a suspected event may be considered a detected event.

FIG. 1 shows a computerized system 100 for monitoring and tracking a tag, said tag associated to a single tool or to a set of tools in one or more location, according to some exemplary embodiments of the subject matter. The tag 104 emits a signal to enable tracking the location of a tool 102 or the set of tools 107. The computerized system 100 comprises a central server 110, which is used to track and monitor the tag 104. The tag 104 is paired to a tool 102. The tag 104 may be an RFID-enabled transmitter or transponder, a barcode, a data matrix (2D), an embedded tag or the like. The tool 102 may be a surgical instrument or a surgical item or a disposable item.

In some exemplary embodiments of the subject matter, the computerized system 100 monitors and tracks the tag 104 which is associated with a tool set 107 rather than a single tool 102. Monitoring of the tool set 107 enables monitoring and tracking several tools that are used as a group during one or more procedures, for example a surgery-specific tool set 107 comprising customized tools for surgery.

The central server 110 is in communication (120) with monitoring stations and tools or sets of tools at different locations via a computerized network 127, which may be a wired and/or wireless communications network that allows computers or computerized devices to exchange data over various communication protocols such as IP (Internet Protocol), cellular, radio, satellite, optical fibers, cables, etc. The computerized network 127 may be or may include an IP network, a local area network, a wide area network, a remote network, a web-based network, a cloud-based network, a Virtual Private Network (VPN), etc.

Each entity or location e.g. Hospital A 121, Hospital B 122, Reprocessing Facility 123, Surgical Instrument Manufacturer 137 and/or regulatory body 136 may communicate (120) with central server 110 via network 127. In some embodiments, monitoring stations located across various locations may communicate directly with each other, and not necessarily via central server 110. For example, a monitoring station 124 in Hospital A 121 may communicate directly with a monitoring station 124 located in the facility of Surgical Instrument Manufacturer 137.

Each entity or location 121, 122, 123, 136 and/or 137, may include one or more signal receiving units 128, e.g. antennas, barcode readers, Wi-Fi stations, or any other hardware and/or software which may be used to receive, store and transmit location and identification data relating to a tag paired to a tool. Signal receiving unit 128 may one or more fixed or mobile antennas or other signal receiving units, as indicated by dashed lines 129. The signal receiving unit 128 detects and receives a signal 106 emitted by the tag 104 when the tag 104 is near the signal receiving unit 128, e.g. within a predetermined range or radius from the signal receiving unit 128. The signal receiving unit 128 transmits the signal received from the tag 104 to the central server 110, e.g. directly, or via a monitoring station 124 to which signal receiving unit 128 is operationally connected. For example, in a medical facility, the signal receiving unit 128 may be located in a tray on which the tool 102 or tool set 107 is placed. When the tool 102 or tool set 107 is placed in close proximity near unit 128, the signal receiving unit 128 receives the signal of the tool 102 or tool set 107 and transmits the signal to a monitoring station 124, which is positioned in a nearby location, e.g. near a surgical operation room in hospital A. The monitoring station 124 may transmit the signal and related data (e.g. location at which it was detected, identity of monitoring station or antenna through which the signal was received, etc.) to the central server 110.

The one or more antennas 128 may be located throughout one or more physical locations, e.g. locations 121-123, 136, 137 which may include various medical facilities, hospitals, reprocessing facilities, or the like. Each antenna or signal receiving unit of the one or more signal receiving units 128 is in communication with or operationally connected to the computerized network 127 or to monitoring station 124, such that the central server 110 receives data relating to location and identification of every tag that comes in vicinity to or predetermined range from the one or more signal receiving units 128.

The central server 110 receiving the signals obtained by the one or more signal receiving units 128 stores a data record of the tag 104 in a tag database (not shown) for tracking and monitoring one or more tags in real time across the one or more locations. The data record stored for the tag 104 comprises information about the associated tool 102 or set of tools 107, such as, the tool 102 identification number or code, or a batch identification number or code for a set of tools, a date/time stamp during which a tag was read by the signal receiving unit 128, current tag location and previous locations, or the like.

Each location 121-123 comprises one or more monitoring stations, illustrated as instances of a monitoring station 124, representing any number of monitoring stations 124, as indicated by dashed lines 125. The monitoring station 124 is positioned within the hospital or facility location along key locations where the tool 102 or tool set 107 is transferred through, stored, maintained, sanitized, or the like.

The monitoring station 124 is a computerized device that enables a user of the monitoring station 124 to input usage data about the tool 102 or tool set 107. For example, the usage data may be or may include a flag event that the user inputs into the monitoring station 124. Monitoring station 124 may typically be a personal fixed or mobile computer or workstation, which may include standard components such as a processor, a memory or storage unit, a disk drive, a monitor, and input-output devices, although alternate configurations are possible. The monitor, for example, may be a conventional video display, but may, in addition, be any other device capable of providing image, stream of images or other data.

Instructions or software for carrying out a method according to an embodiment of the invention may be included as part of monitoring station 124 and as part of central server 110, for example stored in a storage unit operationally connected to or included within central server 110 or monitoring station 124.

A non-exhaustive list of examples of a storage unit may include any combination of the following: semiconductor devices such as registers, latches, electrically erasable programmable read only memory devices (EEPROM), flash memory devices, non-volatile random access memory devices (NVRAM), synchronous dynamic random access memory (SDRAM) devices, static random access memory (SRAM), universal serial bus (USB) removable memory, compact flash (CF) memory cards, personal computer memory card international association (PCMCIA) memory cards, security identity module (SIM) cards, optical devices, such as compact disk read-write memory (CD ROM), and/or magnetic devices, such as a hard disk, a floppy disk, a magnetic tape, and the like.

Embodiments of the invention may include an article such as a computer or processor readable medium, or a computer or processor storage medium, such as a memory, a disk drive, or a flash memory to encode, include or store instructions, e.g., computer-executable instructions, which when executed by a processor or controller, carry out methods disclosed herein.

A flag event, or flag event data, as referred to in the context of the present application, may be a data bundle or data set, and may include an indication and/or a notification that at least one event of a predetermined list of events has occurred, e.g. an infection control event or other perioperative detected event which are monitored and regulated. The flag event may include data relating to a tool 102 or tool set 107 which were present at the location of the detected event, during the time the detected event occurred. The flag event may be in the form of a data file, a message, a data record, or other data structure, and may be generated or updated after receiving an indication or detection of an occurrence of a detected event. For example, a tool 102 may have been used during a surgery, and at a later point in time (e.g. hours or days after the surgery) it may be determined that the patient who participated in the surgery is a carrier of CJD. Determination of a patient carrying CJD may be considered a detected event. If the tool 102 has not been properly maintained and disinfected according to a specific set of required actions pertaining to detection of a CJD detected event, it may transmit CJD to future patients or staff 108 (e.g. handling staff, reprocessing staff, or medical staff) at a next location where the tool 102 or tool set 107 is used or maintained.

The flag event may include tag identity data and detected event data, for example relating to a maintenance procedure that was not performed or was improperly performed, thus indicating to a later user of the tool 102 which necessary actions or maintenance procedures the tool must undergo to be fit for use. The flag event data is used to update the status of the associated tool 102 or tool set 107, and enables the central server 110 to notify relevant entities that mitigate detected events. For example, the central server 110 may send a notification or alert to a hospital, a regulatory body, manufacturer, reprocessing facility, or the like. In some cases, the central server 110 may send an instruction to an entity that is transferring or delivering the tool 102/tool set 107, to reroute the tool 102/tool set 107 from an original destination to a maintenance location. In some cases, matching the flag event to the tool 102/tool set 107 may include executing a predetermined set of commands which may be stored, for example, in a storage unit which is operationally connected to central server 110. A list of predetermined detected event types may be defined, and for each event type, a certain set of instructions or a certain protocol may be followed.

Detected event types may include, but are not limited to, detection and/or suspicion of a hazardous disease during and/or after a medical procedure, detection of a tool defect, missing surgical loaner set, detection of abnormal use of a tool, detection of abnormal handling of a tool or tool set, detection that a tool or set were released before sterilization test result which eventually ended with failure was available, inappropriate maintenance, inappropriate sanitation, or any other abnormal event which may require handling the participating tools according to a specific protocol or according to a predetermined stored action set or instruction set. For example, in a case of detection of a tool defect, the manufacturer of the tool may be notified. In other cases, operations related to matching the flag event to the tool 102 or tool set 107 may be performed by the user who input the flag event to the monitoring station 124. For example, an operation may include notifying an appropriate entity of the detected event, e.g., notifying a government agency of an identified CJD infection event so as to comply with regulatory guidelines, notifying the people who handled the tool since the event occurred, notifying that the tool is unfit for use, and notifying a sterilization facility which procedures the tool must undergo in order to return to standard use.

For each detected event type, a certain set of rules or actions required to mitigate the detected event type may be stored, for example in a storage unit operationally connected to server 110, and/or in a tag database. The set of rules may include, for example, a list of people, locations, or entities that need to be informed of the occurrence of a flag event of a certain type, a list of operations that need to be performed in order to handle the detected event that triggered the flag event, where the tools need to be sent, whether the tools should be disposed of, etc.

When a flag event is inputted into a monitoring station 124 after the tool 102 or tool set 107 has left the location at which the monitoring station 124 is located, the flag event must be transmitted to a current location of the tool to alert any future user of the tool. The flag event is transmitted to the central server 110 from the monitoring station 124, via network 127.

The central server 110 determines the current location data of the tool 102 or tool set 107 according to the most recent signal received from a signal receiving unit 128, which obtained the signal transmitted by tag 104 paired to the tool 102 or to tool set 107. The signal receiving unit 128 obtains the signal 106 from the tag 104 each time the tag 104 is within the reception range of the signal receiving unit 128. The signal receiving unit 128 and/or monitoring station 124 transmits to the central server 110 a notification of receiving the signal 106. The central server 110 stores the location of the signal receiving unit 128 as the updated location of tag 104 in the tag database, thus maintaining an accurate and current record of the location in the tag database, and a log of all the locations of the tag according to the time the location was detected by a signal receiving device 128, e.g. an antenna. The central server 110 transmits the flag event to the monitoring station 124 at the current location of the tool 102 to enable suitable treatment of the tool 102 or tool set 107 according to data of the flag event.

In case of a flag event obtained for a tool set 107, it is required to determine current location of each tool within the tool set 107 that participated in the procedure that caused inputting the flag event, since a tool set may not maintained as a single group after a specific use. Thus, a current location of each of the tools belonging to tool set 107 must be obtained and its users alerted. The group of tools which were associated with set 107 at the time of the procedure that caused the flag event may be determined by central server 110 according to the maintained usage history stored in the tag database for each tool within set 107.

In some exemplary embodiments of the subject matter, the central server 110 records the movements of the tool 102 or the set of tools 107 to and from different locations. The central server 110 determines which tool 102 and/or set of tools 107 and/or staff 108 was present in the event location during the time of the event. The central server 110 collects all data records of tags, for example the tags are registered to be tracked through the central server 110. The central server 110 communicates with multiple locations, i.e. hospitals, medical facilities, manufacturers, retailers, etc. in order to match the tag 104 with the event, and send the required instructions and/or notifications according to the detected event type.

Figure 2:
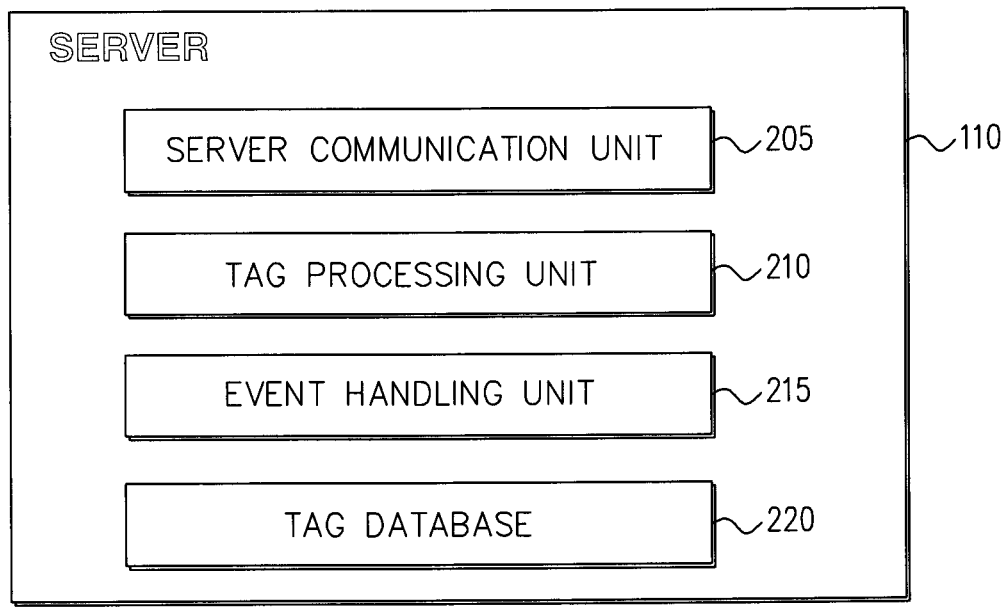
FIG. 2 shows a server, according to some exemplary embodiments of the subject matter.

FIG. 2 shows a central server 110, according to some exemplary embodiments of the subject matter. The central server 110 comprises a server communication unit 205, which may include for example a transceiver and a processor, receives and transmits data across the computerized network 127 of FIG. 1. The server communication unit 205 receives location data and/or identification data from the one or more signal receiving units 128 of FIG. 1, e.g. based on the signal from the tag 104. The location data comprises a tag unique identification code (UID), which is used to identify the tag 104, and data relating to the receiving antenna's identification or location. The location data may further include a time stamp or time period during which the tag was identified at the signal receiving unit 128.

The central server 110 comprises a tag processing unit 210, which determines a location of the tag 104. The location of the tag 104 is determined by the tag processing unit 210 according to, for example, a known location of the antenna of the one or more signal receiving units 128 that receives the signal (e.g. RFID signal) of the tag's UID and transmits the signal to a monitoring station which is in data communication with the antenna. The location data is then transferred from the monitoring station to the central server 110, e.g. using wired or wireless communication methods as known in the art. In some embodiments, the location data may be transmitted directly from the signal receiving unit 128 to the central server 110. For example, each antenna of the one or more signal receiving units 128 is identified by a unique IP address according to which the tag processing unit 210 determines the location of the signal receiving unit 128. According to the tag UID and location of the signal receiving unit 128, the tag processing unit 210 determines the location of the tag 104.

The central server 110 comprises an event handling unit 215, which processes data records which store information related to flag events. The server communication unit 205 receives the flag event data from a monitoring station 124 of FIG. 1. The event handling unit 215 determines a tag UID for which the flag event was received, and proceeds to handle the flag event according to a stored set of actions, operations or instructions which are associated with the detected event type that was received. The stored set of actions may be stored in server 110, e.g. in tag database 220 or in a storage unit which may be operationally connected to the server 110. The stored set of actions may include, for example, determining to which location or multiple locations a notification of the flag event must be sent, e.g. based on current and/or previous locations of the tool 102 or tools set 107 of FIG. 1 and the tag 104. The stored set of actions may include determining which people handled the tool associated with the flag event. For certain detected event types, it may be required to notify each person that handled the tool, and requiring each person to undergo a certain examination or procedure.

The event handling unit 215 further performs removal of the flag event (e.g. marks the flag event status as completed or inactive), when a flag removal event is received by the central server 110, e.g. from a monitoring station 124 of FIG. 1, or from another device connected to computerized network 127 of FIG. 1. After the tool 102 is handled according to the stored set of actions defined for the flag event, a user of a monitoring station 124 at the location at which the tool 102 or tool set 107 was treated may input a flag removal event.

For example, after a certain flag event is identified, a certain operation or stored set of operations may be required in order to allow the tool to be returned to use. In one example, it may be determined that the tool 102 requires sterilization using ethelyne oxide. A monitoring station 124 receives a notification associated with the flag event, which may include data relating to this requirement. Once the sterilization is performed, a user of monitoring station 124 inputs data for the flag removal event, to delete or remove the flag event from the list of active flag events which central server 110 may store. The flag removal event is transmitted from a monitoring station 124 to the central server 110, which removes the flag event from a list of active flag events, and/or from relevant data records in the tag database, or marks the flag event data records with an appropriate status, e.g. "complete", "inactive", "disregard with supervisor approval", "postpone with supervisor approval", etc.

In another example a detected event requires a tool to be destroyed or discarded due to various reasons such as end of life, malfunction that cannot be fixed, severe contamination or high risk of severe contamination, etc. Destroying or discarding a tool may be provided to a user as a set of instructions, e.g. step-by-step instructions.

In some embodiments, only users with specified permissions may be allowed to input a flag removal event. The flag removal event may include determining if the stored set of actions was properly and fully performed. A log of the actions may be stored in a data record which details the operations performed with relation to the flag event, for example in tag database 220 or in another storage unit connected to server 110.

The central server 110 comprises a tag database 220, which stores data records for each tag UID, and include information such as time-based location history, current location of the tag, flag events which were associated with the tag UID, and other usage or maintenance data relating to a specific tag. The tag database 220 may store data records related to the monitored tools, for matching or correlating between events that relate to the tool 102 or set of tools 107. The central server 110 may be configured to communicate with monitoring stations in various locations and to retrieve or provide information related to a flag event or a tool 102. The central server 110 obtains information or data related to flag events which may be reported from multiple locations, associates each flag event to a tool 102 or set of tools 107 which were located in the same location during the time duration of the event (e.g. during at least a portion of the event duration), and matches existing and previous locations of the relevant tool 102 or set of tools 107 to a specific event.

Figure 3:
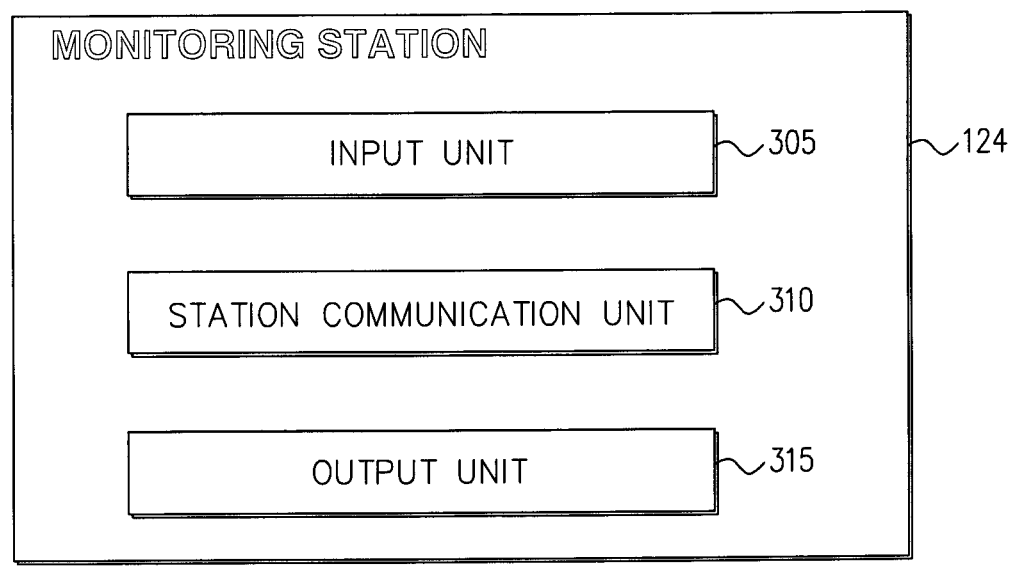
FIG. 3 shows a monitoring station according to some exemplary embodiments of the subject matter.

FIG. 3 shows a monitoring station, according to some exemplary embodiments of the subject matter, e.g. monitoring station 124 of FIG. 1. The monitoring station 124 is a computerized device located at predetermined sites at a certain location or facility. For example, in a medical facility, the monitoring station 124 may be a desktop computer located at a disinfection and sterilization room of a hospital. The monitoring station 124 monitors the performance of the disinfection and sterilization devices and the maintenance of tool 102 of FIG. 1 or tool set 107 of FIG. 1. The monitoring station 124 comprises an input unit 305. In some cases, the input unit 305 may be include a keyboard, a mouse, and/or a touchscreen which enable a user of the monitoring station to input data into the monitoring station.

The monitoring station 124 comprises a communication unit 310, which transmits data records received by the input unit 305 to the central server 110 of FIG. 1. The communication unit 310 receives the data record from the central server 110.

Monitoring station 124 is used to input flag events which were identified at the location of the monitoring station, using the input unit 305. The monitoring station may continuously or intermittently update a central server (e.g. server 110 of FIG. 1 or 2), when a flag event or a flag removal event is input by a user of monitoring station 124. Monitoring station 124 is further used to notify a current user of a tool or tool set, if a flag event was received for the tool or tool set. The notification, which may include a visual and/or sound notification, may include a list of actions or operations required to be performed by the user who receives the notification.

Figure 4A:
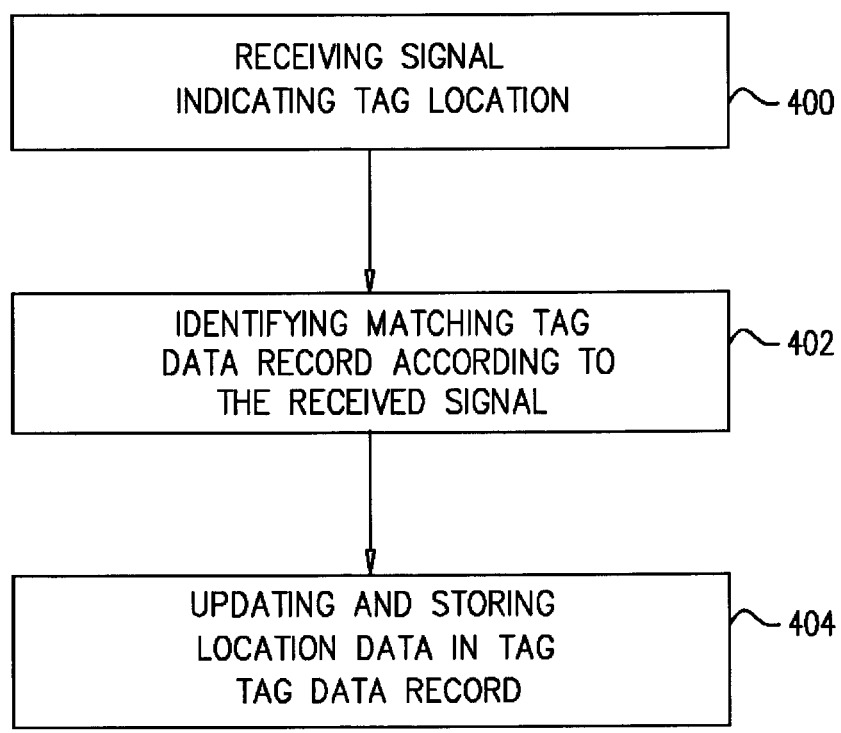
FIGS. 4A-4C show methods performed by a server for monitoring and tracking a tag at one or more locations, according to some exemplary embodiments of the subject matter.

FIG. 4A shows a method for identifying and tracking a location of a tool, according to some exemplary embodiments of the subject matter. Step 400 discloses the central server 110 of FIG. 1 or 2 receiving a signal comprising tag identity data and tag location data from a signal receiving unit 128 or from a monitoring station 124 of FIG. 1. The signal may be transmitted to the central server in real time or substantially in real time, over network 127, for example upon identification of the tag UID in the signal obtained by the signal receiving unit 128. In some embodiments, the signal may be transmitted directly from the signal receiving unit 128 to the central server 110, while in other embodiments the signal may be received by monitoring station 128 and transmitted to the central server. The signal may include data related to the tag and the tool paired to it, for example a tool type, tag identification data, a timestamp and location of the obtained signal, etc.

Step 402 discloses the central server 110 identifying a matching tag data record, e.g. stored in a tag database, according to tag identity data received as part of the signal, such as the tag UID.

Step 404 discloses the central server 110 updating and storing the location data according to the identified tag data record. The central server 110 updates the location and stores the location with the stored data record in a tag database, e.g. tag database 220 of FIG. 2.

Figure 4B:
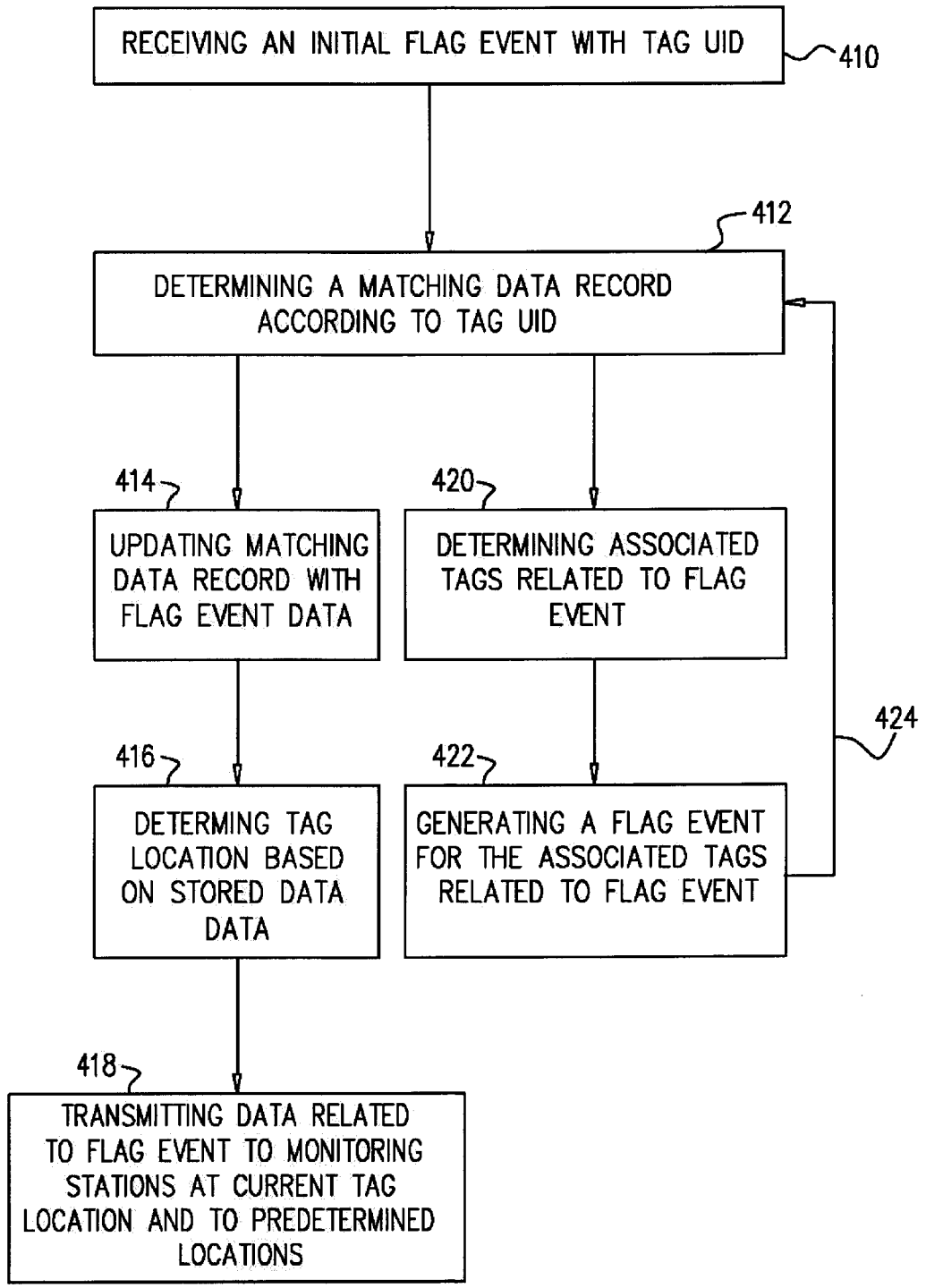

FIG. 4B shows a method for handling a received flag event, according to some exemplary embodiments of the subject matter. Step 410 discloses the central server 110 receiving the flag event. The central server 110 receives the flag event from the monitoring station 124 of FIG. 1. The flag event may include the tag identity data (UID) and event-related data, such as a location of a detected event, name of the facility of the detected event, timestamp and duration of the detected event, an identified contamination source, required maintenance operations to sterilize the tool and prepare it for use, list of places or entities that must be notified of such flag event or the like. The flag event is received when the tool is considered hazardous or contaminated, for example, and was not properly maintained at a previous or current location of the tool 102 of FIG. 1 or tool set 107 of FIG. 1.

For example, the tool 102 or tool set 107 may have been used during a medical procedure (e.g. surgical operation) at a hospital. After the procedure the tool 102 or tool set 107 was required to undergo a disinfecting procedure, however, the disinfecting procedure was not performed and the tool 102 was transferred to a different location to be used in another medical procedure. After the tool 102 or tool set 107 was transferred, a user of the monitoring station 124 may determine that the disinfection procedure was not performed, and may input a flag event into a monitoring station. The flag event, which includes data related to the detected event, may be automatically transmitted to the central server 110, e.g. by a communication unit of the monitoring station.

In step 412, central server 110 may identify or determine a matching data record in a tag database, according to the tag identification data received with the flag event. The flag event comprises a unique tag identification which enables the central server 110 to identify the tag 104 and the tool 102 or tool set 107 for which the flag event is received. The central server 110 matches the received tag identification of the flag event and compares it to the data records stored in the tag database 220 of FIG. 2. For example, the central server 110 determines a matching data record in tag database according to the received tag identification provided along with the flag event data, e.g. a tag UID "1357".

Step 414 discloses the central server 110 updating the matching data record with the flag event data. The data record stored in the tag database may include the tag UID, the current location of the tag 104, previous locations of the tag from the time the event in issue occurred (e.g. a previous operation involving the tag and its respective item/instrument/disposable) and all previous locations it was detected in (until reaching its current location), the tool 102 or tool set 107 associated with the tag 104, or the like.

The flag event data is associated with or used to update the matching tag data record, and includes data relating to the flag event, such as time of occurrence, duration, location of detected event, detected event type (detected infectious disease, improper handling or sanitation, detected tool defect, etc.) and the like.

Step 416 discloses the central server 110 determining the current tag location based on the stored data record. The central server 110 determines the tag location by retrieving the current location stored in the data record based on to the tag UID.

Step 418 discloses the central server 110 transmitting data related to the flag event to the monitoring station 124 of FIG. 1. For example, the central server 110 may transmit visual and/or audio notifications, alerts, actions, operations or instructions required to be performed in order to handle the flag event appropriately, e.g. according to a predetermined set of rules, regulations or predetermined protocols. The transmitted data related to the flag event may include the location and/or processing history of the tools related to the flag event, e.g. throughout their entire life cycle or during a time period defined by the end user or predefined in central server 110. The transmitted data may include a list of people who handled the tool since the occurrence of the detected event, a list of people who participated in the detected event that triggered the flag event, a list of people who should be notified of the flag event, and/or a list of tools which were present in the detected event. Other data and additional data related to the flag event may be transmitted.

For example, the flag event may be transmitted to one or more monitoring stations positioned in the current location of the tool according to the location stored in the data record. The flag event is transmitted to notify the user of the monitoring station 124 that the tool 102 or tool set 107 associated with the tag 104 has to undergo the maintenance procedure that was not performed at a previous location, and that use or handling of the tool 102 or tool set 107 prior to performing the maintenance procedure is forbidden.

The central server 110 may, in addition, transmit data related to the flag event to predetermined locations that must be notified of occurrence of the detected event that caused a flag event, e.g. immediately or shortly after the flag event is received at the central server 110. For example, the data related to the flag event may be transmitted to a regulatory body, and/or the manufacturer of the tool. In some exemplary cases, data related to the flag event may be transmitted to a transition vehicle, for example a truck in route transferring the tool 102 or tool set 107 from a first location to a second location may receive indication of the flag event. When a driver of the truck receives the flag event indication, the data related to the flag event may include information of the location to which the truck must divert in order to handle the flag event appropriately, e.g. in order to deposit the tool 102 or tool set 107 for treatment and any other instructions related to safety while handling a tool which is associated with flag event.

Step 420 discloses the central server 110 determining associated tags (e.g. according to the tag UID) related to the flag event, based on the UID of the tag. Associated tags related to a flag event may include tags connected to tools which came in contact with the contaminated tool during or after the detected event that triggered the flag event, or which were present at the time and location of the detected event that triggered the flag event (e.g. were used in the same medical procedure, or situated on the same table, etc.).

In some non-limiting embodiments, a tool set 107 comprising multiple tools may be used during a medical procedure, thus the tool set 107 may undergo maintenance procedures jointly, in a group or a batch. If a certain procedure was determined at a later time as a detected event triggering a flag event (e.g., the patient was identified at a later stage as carrying CJD), this creates a situation where the set of tools did not receive the necessary maintenance procedure and the tools belonging to that set are not safe for use. Furthermore, tools that came in contact with the tool 102 tool set 107 at a secondary or third location may also require a maintenance procedure due to possible indirect contamination that may be caused by coming in contact with the tool 102 prior to its sterilization or maintenance.

The central server 110 determines the associated tags related to the event flag according to time data and location data history of each tag, stored in the tag database. When the location of a candidate tag is identical to a location of the flag event, and the time period or time range that the candidate was located in the location of the flag event is at least partially overlapping to time period of the flag event, the candidate tag is determined to be associated with the flag event, and a flag event is generated for each of the identified associated tags. The flag event generated for the associated tags is generated with the same location and time data as the detected event that triggered the initial flag event. Arrow 424 indicates that for each associated tag, the procedure of steps 412-418 is repeated. For example, the data records of the associated tags are updated with the flag event, and required notifications, alerts and set of actions or operations are generated for the tool connected to the associated tag.

Figure 4C:
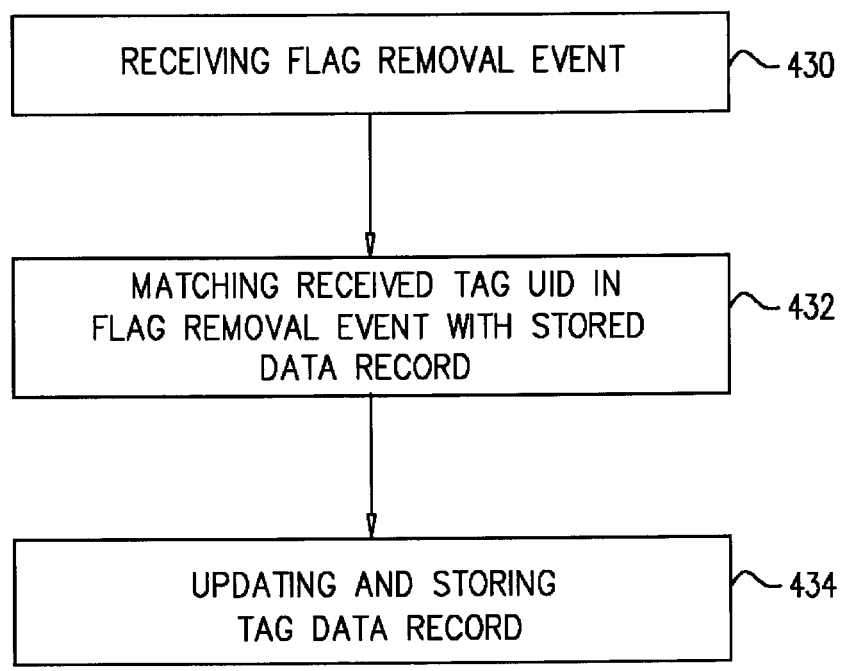

FIG. 4C discloses a method for removal of the flag event, according to some exemplary embodiments of the subject matter. Step 430 discloses the central server 110 receiving a flag removal event. The flag removal event may be input by a user of a monitoring station 124, for example via a software user interface displayed on an output unit or a monitor of the monitoring station. The flag removal event is transmitted to central server 110 (for example by a transmission or communication unit of the monitoring station). The flag removal event indicates that the flag event is to be removed, deleted, or marked as "complete", "inactive" or any other relevant status in the tag database 220 of FIG. 2.

In some embodiments, a flag removal event may be generated by authorized personnel only. For example, a group of specific users may be determined as having suitable permission to generate a flag removal event, and the monitoring station 124 may enable or allow inputting a flag removal event only if an authorized user is logged into the monitoring station. For example, only users registered as belonging to a regulatory body may be allowed to input a flag removal event. In other embodiments, the flag removal event may be input according to the detected event type. For example, if the detected event type is a mechanical defect, only a user belonging to a manufacturing facility, a reprocessing facility or a maintenance facility may input the flag removal event. In another example, if the detected event type is inappropriate maintenance or inappropriate sanitation, only a user belonging to a reprocessing facility may input the flag removal event.

Step 432 discloses the central server 110 matching the received tag identification in the flag removal event with the matching data record stored in the database 220. The flag removal event may include an indication to central server to update tag data records in the tag database which are associated with the specific flag event, that the flag event has been properly handled. The tag identification data is transmitted to central server 110, e.g. the tag UID, as part of the flag removal event, and enables the central server 110 to identify the tag 104 and the tool 102 or tool set 107 for which the flag removal event is received.

Step 434 discloses the central server 110 updating and storing the updated tag data record. The central server 110 removes the flag event from the data record, for example by deleting the flag event data, changing the flag event status to "completed" or "inactive", or otherwise indicating in the data record that the flag event has been properly handled. The updated data record in the tag database 220. For example, the central server may store a list of actions or a set of instructions which were performed in order to mitigate the flag event. Other data relating to the mitigation and handling of the flag event may be provided as part of the flag removal event. One or more processing units, e.g. in monitoring station 124 and/or in central server 110, may be configured to perform the steps of removing a flag event.

Figure 5A:
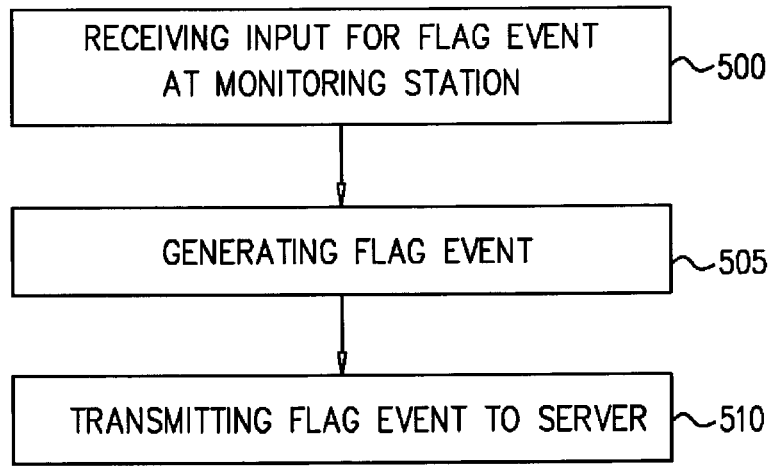
FIGS. 5A-5B show methods performed by a monitoring station for tracking a tag at a location, according to some exemplary embodiments of the subject matter.

FIG. 5A shows a method performed by a monitoring station for generating a flag event, according to some exemplary embodiments of the subject matter. Step 500 discloses the monitoring station 124 of FIG. 1 obtaining input to generate a flag event. The monitoring station 124 is located in a facility such as a hospital, a medical facility or a reprocessing facility, at predetermined locations. For example, in a hospital or medical center, the monitoring station 124 may be located in a disinfection and sterilization room, where tools are disinfected and sterilized after medical procedures.

When tools are used in medical procedures, post-procedure maintenance is critical for safety and maintenance of the tools' quality. Different medical procedures require different maintenance procedures, e.g. disinfection and sterilization procedures. At a monitoring station 124, a user of the monitoring station moderates and oversees that maintenance procedures are performed correctly. In some cases, a procedure may be performed improperly or not according to standards, requirements, or regulations, thus a tool 102 or tool set 107 of FIG. 1 must undergo the maintenance procedure again.

The user of the monitoring station 124 inputs data required for generating a flag event. For example, the input data may include tag identification data (e.g. tag UID), one or more maintenance procedures that tool 102 must undergo, the time and location of the detected event procedure that caused the generation of the flag event, the names of people who may have participated in the procedure, handled tools which were present in the procedure, or people and entities who must be informed of the flag event, and the like. In some cases, a user may be informed that in a previous medical procedure, an infectious disease was identified. Such information may cause the user to input data to generate a flag event relating to the tool 102 and/or to the medical procedure, including the time of occurrence, the location of occurrence, the detected event type, and other related data.

Step 505 discloses the monitoring station 124 generating the flag event. The monitoring station 124 station creates the flag event according to the input data provided by the user. The generated flag event may be a data bundle, for example a file, a mail message, an instant message, a data record, or any other data structure, that includes the provided input data, and other data which may be added, e.g. automatically by a processing unit of the monitoring station (for example, location data indicating location of the monitoring station, time period or duration of the detected event that triggered the flag event, time of inputting the flag event data by the user, the procedure that triggered generation of the flag event, etc.). The data bundle may be stored in a storage unit operationally connected to the monitoring station.

Step 510 discloses the monitoring station 124 transmitting the flag event to the central server 110 of FIG. 1. The monitoring station transmits the data bundle which includes the flag event data to the central server 110, which further transmits the flag event data to a current location of the tool 102 as disclosed in FIG. 4B above, in order to alert the current user of the possible risk and the required mitigation. In addition or instead, central server 110 may transmit the flag event data, or portions thereof, to other locations or entities (e.g. people or users of the computerized system 100) according to a predetermined set of rules or instructions for handling the flag event.

Figure 5B:
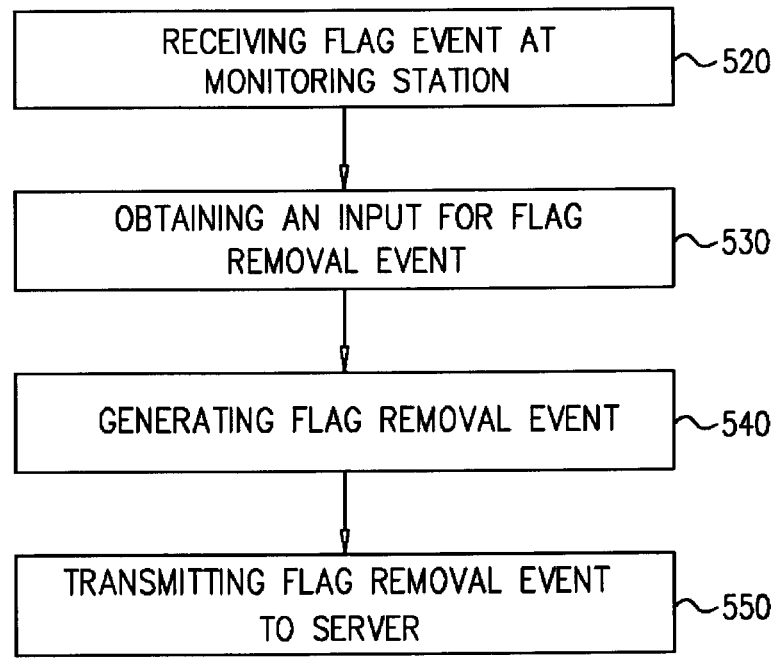

FIG. 5B shows a method performed by the monitoring station 124 for removing the flag event, according to some exemplary embodiments of the subject matter. Step 520 discloses the monitoring station 124 receiving the flag event from the central server 110. The flag event data is received by the monitoring station 124, and causes the monitoring station to provide an alert, e.g. a visual and/or audio alert to a user of monitoring station 124, to notify that the tool 102 should not be used before certain instructions are performed.

Step 530 discloses the monitoring station 124 obtaining the input for a flag removal event. A user of monitoring stations 124 provides input data for generating the flag removal event. The input data may include information about the actions or procedures performed to comply with the set of rules for handling the flag event. For example, the set of rules for handling the flag event required the tool 102 or tool set 107 to be disinfected according to post-surgical procedures. The input may include data relating to the procedures that were performed, e.g. time and location of the disinfection procedure. In some cases, the set of rules for handling the flag event may include discarding the tool 102 or tool set 107, in which case the flag removal event may include data indicating that the tool 102 has been disposed of.

The input data comprises tag identification data, e.g. tag UID, to identify for which tag 104 of FIG. 1 the flag removal event is generated, and to enable the central server 110 to handle the flag removal event.

Step 540 discloses the monitoring station 124 creating the flag removal event. The monitoring station 124 creates the flag removal event with the information identifying the tag 104 for which the flag removal event is created and that the flag event is to be removed.

Step 550 discloses the monitoring station 124 transmitting the flag removal event to the central server 110. The flag removal event is transmitted by the monitoring station 124 to the central server 110 for removal of the flag event from the tag database 220. Removal of the flag event may include, for example, deleting the event from a list of active flag events in tag database 220 of FIG. 2, indicating or marking the data record in the tag database as "inactive" or "completed", or otherwise marking the event as concluded. The removal of the flag event may further include the server 110 transmitting notifications to certain entities that the flag event is now marked as "completed".

While the disclosure has been described with reference to exemplary embodiments, it will be understood by those skilled in the art that various changes may be made and equivalents may be substituted for elements thereof without departing from the scope of the subject matter. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this subject matter, but only by the claims that follow.

The invention claimed is:

1. A computerized system to track and monitor a tag paired to a tool comprising:
   one or more signal receiving units to communicate with a tag;
   a central server comprising
      a tag database configured to store a data record of the tag, wherein the data record comprises information about the tag and a current location of the tag, wherein the current location of the tag is determined by the location of the signal receiving unit which communicated with the tag; and
      a tag processing unit configured to update the data record stored in the tag database;
   one or more monitoring stations each connected to one or more signal receiving units to receive the current location of the tag from the signal receiving units and update the central server; additionally the monitoring stations are configured to enable a user to input a flag event related to the tag, wherein the flag event includes accepting a time of a detected event, tag identification data and an indication that the tool paired to the tag was present at the detected event, and to transmit the flag event to the central server;
   wherein the central server is configured to determine from the records in the tag database one or more tags associated with the identity data of the tag of the flag event, wherein associated tags include tags which participated in the detected event and tags that were in contact with or participated in procedures with the tag of the flag event from the time of the detected event at any previous locations the tag was detected in until reaching its current location; and
   wherein the central server is configured to transmit the flag event data or portions thereof to the monitoring station connected to the signal receiving unit at a current location of the tag of the flag event and the current locations of the one or more associated tags, based on the current locations of the associated tags stored in the tag database.

2. The computerized system of claim 1, further comprising a communication unit to transmit the flag event to a current location where the tag is located.

3. The computerized system of claim 1, wherein the tag is paired to a tool set.

4. The computerized system of claim 1, wherein the signal receiving unit comprises
   an antenna for obtaining the location of the tag, wherein the tag is an RFID enabled transponder paired to at least one tool, wherein the antenna receives a signal transmitted from the tag, the signal comprising tag identity data.

5. The computerized system of claim 1, wherein the tag processing unit is configured to determine a current location of a staff member who participated in a detected event.

6. The computerized system of claim 1, wherein the detected event includes detecting that the tool that is paired to the tag participated in a procedure on a patient having a hazardous disease, which requires additional handling that was not performed on the tool.

7. The computerized system of claim 1, wherein the detected event includes detecting that the tool that is paired to the tag participated in an infection control event, which requires additional handling that was not performed on the tool.

8. A method of tracking and monitoring a tag paired to a tool, comprising:
   receiving at a monitoring station a signal including location data related to the tag from a signal receiving unit at the location of the tag, wherein the signal comprises tag identification data; and wherein the location of the tag is determined by the location of the signal receiving unit which communicated with the tag;
   storing the received location data in a tag database at a central server as of a data record relating to the tag, based on the tag identification data;
   receiving a flag event for the tag, wherein the flag event s input by a user at the monitoring station, and wherein the flag event comprises a time of a detected event, tag identification data, the flag event including an indication that. the tool paired to the tag was present at the detected event;
   determining at the central server one or more tags associated with the received tag identity data, wherein associated tags include tags which participated in the detected event and tags that were in contact with or participated in procedures with the tag of the flag event from the time of the detected event at any previous locations die tag was detected in until reaching its current location;
   transmitting the flag event data or portions thereof to monitoring stations connected to signal receiving units at the current locations of the tag which is retrieved from the stored data record and the one or more associated tags, based on the current locations stored in the tag database.

9. The method of claimed 8, further comprising:
   updating the tag data record stored fit the tag database with the event flag data.

10. The method of claim 8, further comprising updating other tag data records with the flag event data in the tag database.

11. The method of claim 8, further comprising:
   receiving a flag removal event at the monitoring station that is connected to the signal receiving unit at the current location of the tag to remove a flag event from the tag data record, wherein the flag removal event comprises tag identification data;
   updating, the tag data record stored in the tag database according to the flag removal event.

12. The method of claim 8, wherein the signal is received from an antenna that obtains RFID signal of tags paired to at least one tool.

13. The method of claim 8, wherein the flag event is received from a computerized monitoring station.

* * * * *